United States Patent
Schwarcz et al.

(10) Patent No.: US 9,260,394 B2
(45) Date of Patent: Feb. 16, 2016

(54) DERIVATIVES OF NICOTINIC ACID N-OXIDE, THEIR PREPARATION AND THEIR USE AS INHIBITORS OF ENZYME 3-HYDROXYANTHRANILATE-3, 4-DIOXYGENASE

(75) Inventors: Robert Schwarcz, Baltimore, MD (US); Gabriele Costantino, Medesano (IT); Laura Amori, Sassoferrato (IT)

(73) Assignees: UNIVERSITY OF MARYLAND, BALTIMORE, Baltimore, MD (US); UNIVERSITA' DELGI STUDI DI PARMA (IT)

( * ) Notice: Subject to any disclaimer, the term of this patent is extended or adjusted under 35 U.S.C. 154(b) by 223 days.

(21) Appl. No.: 13/979,517

(22) PCT Filed: Jan. 19, 2011

(86) PCT No.: PCT/EP2011/050670
§ 371 (c)(1),
(2), (4) Date: Jul. 12, 2013

(87) PCT Pub. No.: WO2012/097869
PCT Pub. Date: Jul. 26, 2012

(65) Prior Publication Data
US 2013/0289081 A1     Oct. 31, 2013

(51) Int. Cl.
*C07D 213/89*     (2006.01)
*A61K 31/455*     (2006.01)

(52) U.S. Cl.
CPC ........... *C07D 213/89* (2013.01); *A61K 31/455* (2013.01)

(58) Field of Classification Search
None
See application file for complete search history.

(56) References Cited

PUBLICATIONS

Taylor et al. (Contribution from the Noyes Chemical Laboratory, University of Illinois, p. 1633-1640, 1954).*
Amori, Laura et al. On the relationship between the two branches of the kynurenine pathway in the rat brain in vivo. J Neurochem (2009) 109:316-25.
Foster, Alan C. et al. Synthesis of quinolinic acid by 3-hydroxyanthranilic acid oxygenase in rat brain tissue in vitro. J. Neurochem. Jul. 1986; 47(1):23-30.
Guidetti, Paolo et al. Metabolism of [5-3H]kynurenine in the rat brain in vivo: evidence for the existence of a functionalkynurenine pathway. J Neurochem (1995) 65:2621-32.
Heyes, Melvin P. et al. 4-chloro-3-hydroxyanthranilate inhibits brain 3- hydroxyanthranate oxidase. Neurochem Int. 1988; 13(3):405-8.
Linderberg, Mats et al. Synthesis and QSAR of substituted 3-hydroxyanthranilic acid derivatives as inhibitors of 3-hydroxyanthranilic acid dioxygenase (3-HAO). Eur. J. Med. Chem. 34 (1999) 729-744.
Parli, C. John et al. Metabolism of 6-chlorotryptophan to 4-chloro-3-hydroxyanthranilic acid: a potent inhibitor of 3-hydroxyanthranilic acid oxidase. Biochem Biophys. Aug. 1980; 203(1):161-6.
Schwarcz, Robert et al. Quinolinic acid: an endogenous metabolite that produces axon-sparing lesions in rat brain. Science (1983) 219:316-8.
Schwarcz, Robert et al. Manipulation of brain kynurenines: glial targets, neuronal effects, and clinical opportunities. J Pharmacol Exp Ther Oct. 2002; 303(1):1-10.
Todd, William P. et al. Preparation of 4-halo-3-hydroxyanthranilates and demonstration of their inhibition of 3-hydroxyanthranilate oxygenase activity in rat and human brain tissue. Prep Biochem. 1989; 19(2):155-65.
Zadori D. et al. Kynurenines in chronic neurodegenerative disorders: future therapeutic strategies. J Neural Transm. Nov. 2009; 116(11): 1403-9.

* cited by examiner

*Primary Examiner* — Bong-Sook Baek
(74) *Attorney, Agent, or Firm* — Marianne Fulerer; Moore & Van Allen, PLLC

(57) ABSTRACT

A derivative of nicotinic acid N-oxide is described having formula (I): that acts as inhibitor of enzyme 3-hydroxyanthranilate-3,4-dioxygenase (3HAO), and is thus able to reduce QUIN biosynthesis in vivo under excitotoxic or pathological conditions, said compound being at the same time also chemically stable towards auto-oxidation.

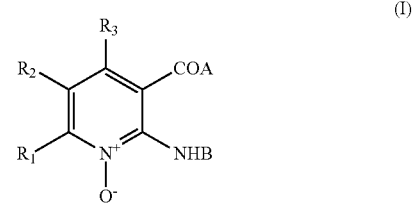

6 Claims, 1 Drawing Sheet

DERIVATIVES OF NICOTINIC ACID N-OXIDE, THEIR PREPARATION AND THEIR USE AS INHIBITORS OF ENZYME 3-HYDROXYANTHRANILATE-3, 4-DIOXYGENASE

CROSS-REFERENCE TO RELATED APPLICATIONS

This application is filed under the provisions of 35 U.S.C. §371 and claims the priority of International Patent Application No. PCT/EP2011/050670 filed on Jan. 19, 2011, the contents of which are incorporated by reference herein for all purposes.

FIELD OF THE INVENTION

The present invention concerns derivatives of nicotinic acid N-oxide, their preparation and their use as inhibitors of enzyme 3-hydroxyanthranilate-3,4-dioxygenase (3HAO), involved in the production, throughout the kynurenine pathway, of quinolinic acid (QUIN), an endogenous neurotoxin.

STATE OF THE ART

The kynurenine pathway of the tryptophan catabolism has attracted a large interest in view of the notion that at least two metabolites throughout the route have sustained neuroactive properties in the central nervous system (CNS). In is particular, kynurenic acid (KYNA) is an allosteric modulator of the glycine site of the NMDA receptor and of the α7 nicotinic receptor, and is endogenous neuroprotective agent, while quinolinic acid (QUIN) is a non selective agonist of the NMDA receptor and has been characterized as a potent neurotoxin, with a marked excitotoxic properties.

Pharmacological approaches finalized at favourably modulating the KYNA/QUIN balance through the inhibition of individual enzymes throughout the kynurenine pathway can be of potential clinical interest in all the conditions characterized by an hyper- or hypo-stimulation of the glutamatergic system (Schwarcz R, Pellicciari R, "*Manipulation of brain kynurenines: glial targets, neuronal effects, and clinical opportunities*" J Pharmacol Exp Ther 2002 October; 303(1): 1-10).

The 3-hydroxyanthranilate-3,4-dioxygenase (3HAO) is the enzyme of the kynurenine pathway which is directly responsible for the conversion of 3-hydroxyanthranilic acid into QUIN, through the intermediate formation of a semimuconic aldeheyde and its subsequent non-enzymatic cyclization (Foster A C, White R J, Schwarcz R, "*Synthesis of quinolinic acid by 3-hydroxyanthranilic acid oxygenase in rat brain tissue in vitro*" J. Neurochem. 1986 July; 47(1):23-30).

Both the enzyme 3HAO and QUIN have been identified in the brain of mammals, including human. QUIN has been extensively characterized as a potent endogenous excitotoxic agent, potentially involved in a series of neurodegenerative disorders and diseases, including Alzheimer's disease, Huntington's disease, cerebral ischemia, HIV-related dementia (Zádori D, Klivényi P, Vámos E, Fülöp F, Toldi J, Vécsei L, "*Kynurenines in chronic neurodegenerative disorders: future therapeutic strategies*" J Neural Transm. 2009 November; 116(11): 1403-9).

3HAO inhibitors, with the potentiality of restoring physiological levels of QUIN under pathological conditions, may find a clinical application in all the conditions characterized by an excessive QUIN production.

In the past, 3HAO inhibitors have been identified through the substrate analogue approach. Thus, in 1980, 4-chloro-3-hydroxyanthranilic acid, a metabolite of 6-chlorotryptophan, was reported as a potent inhibitor of 3HAO (Parli C J, Krieter P, Schmidt B, "*Metabolism of 6-chlorotryptophan to 4-chloro-3-hydroxyanthranilic is acid: a potent inhibitor of 3-hydroxyanthranilic acid oxidase*" Biochem Biophys. 1980 August; 203(1):161-6). These data were further confirmed in Heyes M P, Hutto B, Markey S P, "*4-chloro-3-hydroxyanthranilate inhibits brain 3-hydroxyanthranate oxidase*" Neurochem Int. 1988; 13(3):405-8. In 1989, the reported activity of 4-chloro-3-hydroxyanthranilic acid was extended to other 4-halogen-substituted derivatives of 3-hydroxyanthranilic acid, including 4-fluoro- and 4-bromo-, which showed an inhibitory potency comparable with that of 4-chloro-3-hydroxyanthranilic acid (Todd W P, Carpenter B K, Schwarcz R, "*Preparation of 4-halo-3-hydroxyanthranilates and demonstration of their inhibition of 3-hydroxyanthranilate oxygenase activity in rat and human brain tissue*" Prep Biochem. 1989; 19(2):155-65).

In 1999, Linderberg et al reported a series of 4,5-disubstituted, 4,6-disubstituted, and 4,5,6-trisubstituted analogs of 3-hydroxyanthranilic acid as 3HAO inhibitors in rat brain homogenates (Mats Linderberg, Sven Hellberg, Susanna Björk, Birgitta Gotthammar, Thomas Högberg, Kerstin Persson, Robert Schwarcz, Johan Luthman, Rolf Johansson, "*Synthesis and QSAR of substituted 3-hydroxyanthranilic acid derivatives as inhibitors of 3-hydroxyanthranilic acid dioxygenase (3-HAO)*" Eur. J. Med. Chem. 34 (1999) 729-744).

All the inhibitors described in the literature above reported are able to reduce the QUIN biosynthesis through inhibition of 3HAO, and some of them, particularly 4,6-dibromo-3-hydroxyanthranilic acid, known as NCR-631, have shown this ability in vivo, in addition to anticonvulsivant properties in pharmacologically induced seizures and neuroprotective properties in models of anoxia in organotypical cultures of rat hippocampus.

However, it should be note that the 3-hydroxy-anthranilic acid derivatives so far used as 3HAO inhibitors are intrinsically chemically unstable, due to a tendency to autoxidation of the aminophenol moiety of 3-hydroxy-anthranilic acid.

Therefore, it is an object of the present invention to provide compounds able to inhibit 3HAO and to reduce QUIN biosynthesis in vivo under excitotoxic or pathological conditions, said compounds being at the same time also chemically stable towards auto-oxidation.

SUMMARY OF THE INVENTION

The above object has been achieved by a derivative of nicotinic acid N-oxide of formula (I)

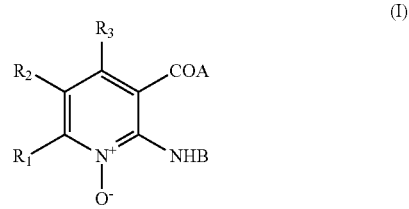

wherein
$R_1$, $R_2$, $R_3$ are, independently of each other, H, halogen, an alkyl group ($C_1$-$C_6$), a heterocyclic or aryl group, where said heterocyclic group is aromatic or aliphatic and comprises at least one heteroatom selected from nitrogen, oxygen or sulphur, or a heterocyclic or aryl group substituted with at least one substituent group selected from $C_1$-$C_3$ alkyl, halogen, —OH, —CN, —COOH, —NO$_2$, —OY1, —COOY1, —NY1Y2, where Y1 and Y2 are, independently of each other, H or $C_1$-$C_3$ alkyl.

A is —OH, —OR$_4$ or —NZ1Z2, where Z1 and Z2 are, independently of each other, H or $C_1$-$C_3$ alkyl, and B is H or R$_5$, where R$_4$ and R$_5$ are, independently of each other, an alkyl group ($C_1$-$C_3$).

As it will be apparent from the following detailed description, it has been in fact surprisingly found that the compounds, subject of the present invention, act as inhibitors of enzyme 3-hydroxyanthranilate-3,4-dioxygenase (3HAO), and at the same time are chemically stable towards auto-oxidation.

In another aspect, the present invention concerns a process for preparing the above derivative of formula (I), comprising the step of:

a) reacting a compound of formula (i)

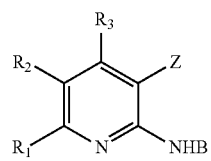

where Z is —COOH, —COOCH$_3$, or —CN, with hydrogen peroxide in presence of methyltrioxorhenium (CH$_3$ReO$_3$).

In a further aspect, the present invention concerns the use of said derivative as inhibitor of enzyme 3-hydroxyanthranilate-3,4-dioxygenase (3HAO) for the treatment of pathologies ascribable to an excessive QUIN production, such as Alzheimer's disease, Huntington's disease, cerebral ischemia, HIV-related is dementia or neonatal hypoxia.

DESCRIPTION OF THE FIGURES

The characteristics and advantages of the present invention will be apparent from the detailed description reported below, from the working Examples given for illustrative and non-limiting purposes, and from the annexed Figures, wherein.

DETAILED DESCRIPTION OF THE INVENTION

Figure 1:
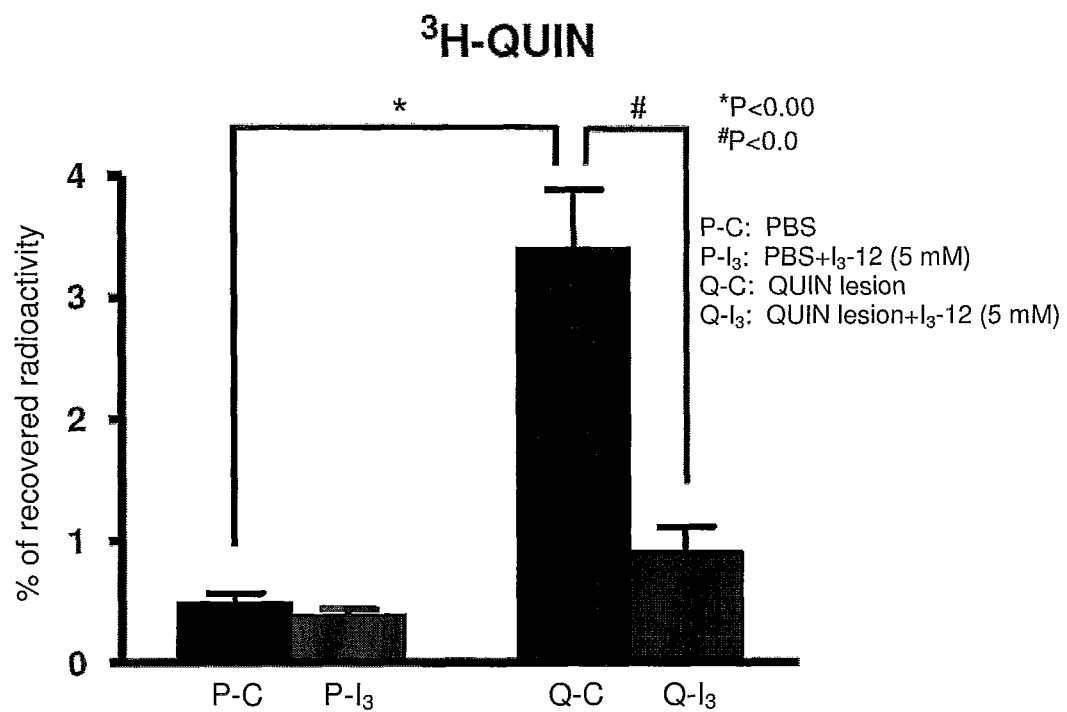
FIG. 1 shows the effect of the compound of Example 3 on the brain level of QUIN after in vivo administration under excitotoxic conditions.

The present invention thus relates to a compound of formula (I):

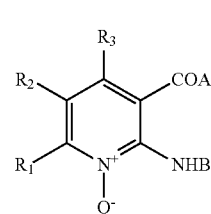

wherein

R$_1$, R$_2$, R$_3$ are, independently of each other, H, halogen, an alkyl group ($C_1$-$C_6$), a heterocyclic or aryl group, where said heterocyclic group is aromatic or aliphatic and comprises at least one heteroatom selected from nitrogen, oxygen or sulphur, or a heterocyclic or aryl group substituted with at least one substituent group selected from $C_1$-$C_3$ alkyl, halogen, —OH, —CN, —COOH, —NO$_2$, —OY1, —COOY1, —NY1Y2, where Y1 and Y2 are, independently of each other, H or $C_1$-$C_3$ alkyl.

A is —OH, —OR$_4$ or —NZ1Z2, where Z1 and Z2 are, independently of each other, H or $C_1$-$C_3$ alkyl, and B is H or R$_5$, where R$_4$ and R$_5$ are, independently of each other, an alkyl group ($C_1$-$C_3$).

In fact, it has been surprisingly found that said compound acts as inhibitor of enzyme 3-hydroxyanthranilate-3,4-dioxygenase (3HAO), and at the same time is chemically stable towards auto-oxidation.

Due to a particular electronic configuration, this compound has shown to be able to competitively interact with 3-hydroxyanthranilic acid in the binding pocket of 3HAO by chelating the catalytically relevant Fe$^{2+}$ ion, thus simulating an intermediate complex between the natural substrate, 3-hydroxyanthranilic acid, and the enzyme's active site. The compound of the invention is therefore able to competitively inhibit 3HAO, thus reducing the QUIN biosynthesis. In vivo, this compound has proved to be able to reduce the extracellular QUIN levels in the CNS of rats which underwent excitotoxic lesions, as reported in Example 9. Importantly, the compound of formula (I) is also chemically stable towards autoxidation reactions.

Preferably, in said compound of formula (I):

R$_1$, R$_2$, R$_3$ are, independently of each other, H, Cl, an alkyl group ($C_1$-$C_3$), or a heterocyclic or aryl group, where said heterocyclic group is aromatic or aliphatic and comprises at least one heteroatom selected from nitrogen, oxygen or sulphur.

A is —OH, or —NH$_2$, and

B is H.

Further preferred are the following compounds:

2-aminonicotinic acid N-oxide (I$_1$)

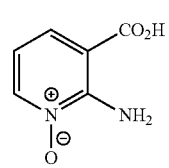

2-amino-6-chloronicotinic acid N-oxide ($I_2$)

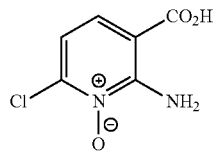

2-amino-6-methylnicotinic acid N-oxide ($I_3$)

2-amino-6-methylnicotinamide N-oxide ($I_4$)

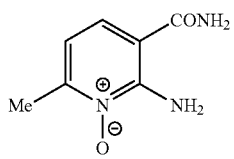

2-amino-4-phenyl-6-methylnicotinic acid N-oxide ($I_5$)

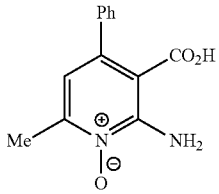

2-amino-4,6-diisopropylnicotinic acid N-oxide ($I_6$)

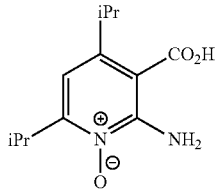

In another aspect, the present invention concerns a process for preparing the above compound of formula (I), comprising the step of:

a) reacting a compound of formula (i)

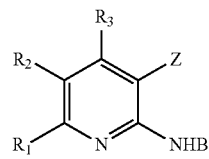

where Z is —COOH, —COOCH$_3$, or —CN,
with hydrogen peroxide in presence of methyltrioxorhenium ($CH_3ReO_3$).

In a further aspect of the present invention, the compound of formula (I) is used as medicament, particularly, as inhibitor of enzyme 3-hydroxyanthranilate-3,4-dioxygenase (3HAO) for the treatment of pathologies ascribable to an excessive QUIN production.

As a matter of fact, as above reported, in vivo, this compound has proved to be is able to reduce the extracellular QUIN levels in the CNS of rats which underwent excitotoxic lesions, as reported in Example 9.

Particularly, said pathologies ascribable to an excessive QUIN production are chronic and/or neurodegenerative disorders such as Alzheimer's disease, Huntington's disease, cerebral ischemia, HIV-related dementia or neonatal hypoxia.

Examples of the present invention are hereinafter provided for illustrative and non-limiting purposes.

EXAMPLES

Example 1

Preparation of 2-aminonicotinic acid N-oxide ($I_1$):

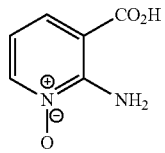

1) A suspension of 2-aminonicotinic acid (833 mg, 6.00 mmol) and potassium carbonate (912 mg, 6.60 mmol) in dimethylformamide (DMF, 8.5 ml) was heated to reflux. The reaction mixture was cooled to room temperature and 415 µl of iodomethane (6.60 mmol) were added. The mixture was then refluxed under stirring for 18 h; after subsequent cooling, the mixture was finally filtered and the filtrate was concentrated under reduced pressure. The crude product was purified is by flash chromatography on silica gel (ethyl acetate/petroleum ether=7/3). The isolated 2-aminonicotinic acid methyl ester was obtained in 58% yield.

2) A catalytic amount of methyltrioxorhenium (MTO, 13 mg, 0.05 mmol) and excess 30% hydrogen peroxide (3 ml) were added to a solution of 2-aminonicotinic acid methyl ester (152 mg, 1.00 mmol) in ethanol (5 ml). The reaction mixture was stirred for 3 h at room temperature. A catalytic amount of manganese dioxide was added to quench the excess peroxide. The mixture was then filtered and the solvent was removed with a rotary evaporator. The crude product was dissolved into water and extracted with methylene chloride. The organic phase was dried over anhydrous sodium sulphate and concentrated at reduced pressure. The crude product was purified by flash chromatography on silica gel (methylene chloride/methanol saturated with ammonia=98/2) thus obtaining 2-aminonicotinic acid methyl ester N-oxide in 63% yield.

3) 1N sodium hydroxide (0.5 ml) was added to a solution of 2-aminonicotinic acid methyl ester N-oxide (80 mg, 0.48 mmol) in ethanol (5 ml) and the reaction mixture was stirred under reflux for 10 h. The solvent was evaporated under vacuum and the residue was taken up with water and extracted with methylene chloride. After addition of 1N hydrochloric acid to the aqueous solution, the resulting precipitate was filtered, rinsed with water and dried under vacuum, thus obtaining 2-aminonicotinic acid N-oxide ($I_1$) as a white solid.

Yield: 47%

$^1$H-NMR (DMSO-$d_6$): δ 6.67 ppm (dd, H, J=6.60, 7.80 Hz), 7.68 ppm (bs, NH$_2$), 7.73 ppm (dd, H, J=0.66, 7.80 Hz), 8.33 ppm (dd, H, J=0.66, 6.60 Hz).

Example 2

Preparation of 2-amino-6-chloronicotinic acid N-oxide ($I_2$):

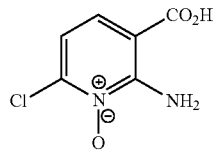

1) A suspension of 2-amino-6-chloronicotinic acid (500 mg, 2.90 mmol) and is potassium carbonate (441 mg, 3.19 mmol) in DMF (5 ml) was heated to reflux. The reaction mixture was cooled to room temperature and 273 μl of iodomethane (4.35 mmol) were added. The mixture was then refluxed under stirring for 18 h. After subsequent cooling, the mixture was finally filtered and the filtrate was concentrated under reduced pressure. The crude product was purified by flash chromatography on silica gel (ethyl acetate/petroleum ether=95/5). The isolated 2-amino-6-chloronicotinic acid methyl ester was obtained in 54% yield.

2) A catalytic amount of MTO (6 mg, 0.02 mmol) and excess 30% hydrogen peroxide (985 μl, 9.65 mmol) were added to a solution of 2-amino-6-chloronicotinic acid methyl ester (90 mg, 0.48 mmol) in ethanol (5 ml). The reaction mixture was stirred for 3 days at room temperature. A catalytic amount of manganese dioxide was added to quench the excess peroxide. The mixture was then filtered and the solvent was removed with a rotary evaporator. The crude product was dissolved into water and extracted with methylene chloride. The organic phase was dried over anhydrous sodium sulphate and concentrated at reduced pressure. The crude product was purified by flash chromatography on silica gel (methylene chloride/methanol saturated with ammonia=50/50) thus obtaining 2-amino-6-chloronicotinic acid methyl ester N-oxide in 45% yield.

3) 1N sodium hydroxide (240 μl) was added to a solution of 2-amino-6-methylnicotinic acid methyl ester N-oxide (44 mg, 0.22 mmol) in ethanol (4 ml) and the reaction mixture was stirred under reflux for 1 h. The solvent was evaporated under vacuum and the residue was taken up with water and extracted with methylene chloride. After addition of 1N hydrochloric acid to the aqueous solution, the resulting precipitate was filtered, rinsed with water and dried under vacuum, thus obtaining 2-amino-6-chloronicotinic acid N-oxide ($I_2$) as a white solid.

Yield: 24%

$^1$H-NMR (DMSO-$d_6$): δ 7.95 ppm (bs, NH$_2$), 7.68 ppm (d, H, J=8.69 Hz), 7.01 ppm (d, H, J=8.69 Hz).

Example 3

Preparation of 2-amino-6-methylnicotinic acid N-oxide ($I_3$):

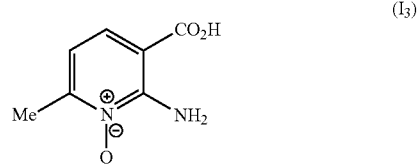

1) 2-chloro-6-methylnicotinonitrile (2.00 g, 13.1 mmol) was dispersed in 12 ml of absolute ethanol, saturated with ammonia, and placed in a high-pressure autoclave. The reaction mixture was heated to 180° C. for 60 h. Then, after cooling to room temperature, the solvent was evaporated under reduced pressure. The crude product was recrystallized from ethanol obtaining 2-amino-6-methylnicotinonitrile in 70% yield.

2) A catalytic amount of MTO (18 mg, 0.075 mmol) and excess 30% hydrogen peroxide (788 μl, 9.01 mmol) were added to a solution of 2-amino-6-methylnicotinonitrile (100 mg, 0.75 mmol) in ethanol (5 ml). The reaction mixture was stirred for 20 h at room temperature. A catalytic amount of manganese dioxide was added to quench the excess peroxide. The mixture was then filtered and the solvent was removed with a rotary evaporator. The crude product was dissolved into water and extracted with methylene chloride. The organic layer was dried over anhydrous sodium sulphate and concentrated at reduced pressure. The crude product was purified by flash chromatography on silica gel (methylene chloride/methanol=98/2) thus obtaining 2-amino-6-methylnicotinonitrile N-oxide in 60% yield.

3) A solution of 2-amino-6-methylnicotinonitrile N-oxide (70 mg, 0.47 mmol) in 6N hydrochloric acid (6 ml) was placed in a microwave tube and irradiated with microwaves (Solvent: aqueous hydrochloric acid; Power: 200 W; Ramp time: 5 min; Heating time: 45 min; Temperature: 85° C.; Pressure: 240 psi; Stirring: on; Cooling: on). At the end of the microwave irradiation cycle, the solvent was removed under reduced pressure. The crude product was washed with water (2 ml) and centrifuged; after removing the supernatant, the precipitate was taken up with methanol and dried, leading to 2-amino-6-methylnicotinic acid N-oxide ($I_3$) in 98% yield.

$^1$H-NMR (DMSO-$d_6$): δ 13.45 ppm (bs, COO—H), 7.73 ppm (bs, NH$_2$), 7.64 ppm (dd, H4, J=2.24, 6.02 Hz), 6.74 ppm (dd, H5, J=2.24, 6.02 Hz), 2.42 ppm (s, CH$_3$).

Example 4

Preparation of 2-amino-6-methylnicotinamide N-oxide (I₄):

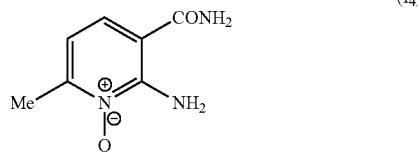

(I₄)

1) 2-chloro-6-methylnicotinonitrile (2.00 g, 13.1 mmol) was dispersed in 12 ml of absolute ethanol, saturated with ammonia, and placed in a high-pressure autoclave. The reaction mixture was heated to 180° C. for 60 h. Then, after cooling to room temperature, the solvent was evaporated under reduced pressure. The crude product was recrystallized from ethanol obtaining 2-amino-6-methylnicotinonitrile in 70% yield.

2) A catalytic amount of MTO (18 mg, 0.075 mmol) and excess 30% hydrogen peroxide (788 μl, 9.01 mmol) were added to a solution of 2-amino-6-methylnicotinonitrile (100 mg, 0.75 mmol) in ethanol (5 ml). The reaction mixture was stirred for 20 h at room temperature. A catalytic amount of manganese dioxide was added to quench the excess peroxide. The mixture was then filtered and the solvent was removed with a rotary evaporator. The crude product was dissolved into water and extracted with methylene chloride. The organic phase was dried over anhydrous sodium sulphate and concentrated at reduced pressure. The crude product was purified by flash chromatography on silica gel (methylene chloride/methanol=98/2) thus obtaining 2-amino-6-methylnicotinonitrile N-oxide in 60% yield.

3) A solution of 2-amino-6-methylnicotinonitrile N-oxide (36 mg, 0.24 mmol) in 30% aqueous ammonia (6 ml) was placed in a microwave tube and irradiated with microwaves (Solvent: aqueous ammonia; Power: 150 W; Ramp time: 1 min; Heating time: 15 min; Temperature: 80° C.; Pressure: 120 psi; Stirring: on; Cooling: is on). At the end of the microwave irradiation cycle, the solvent was removed under reduced pressure. The crude product was purified by flash chromatography on silica gel (methylene chloride/methanol=90/10) thus obtaining 2-amino-6-methylnicotinamide N-oxide (I₄) in 75% yield.

¹H-NMR (DMSO-d₆): δ=8.02 ppm (bs, NH₂), 7.83 ppm (bs, NH₂), 7.60 ppm (dd, H, J=2.24, 6.02 Hz), 6.70 ppm (dd, H, J=2.24, 6.02 Hz), 2.38 ppm (s, CH₃).

Example 5

Preparation of 2-amino-4-phenyl-6-methylnicotinic acid N-oxide (I₅):

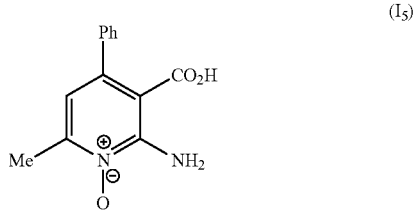

(I₅)

1) Benzaldehyde (406 μl, 4 mmol), acetone (294 μl, 4 mmol), malononitrile (264 mg, 4 mmol) e ammonium acetate (462 mg, 6 mmol) were placed in a microwave tube and irradiated with microwaves (Solvent: none; Power: 150 W; Ramp time: 5 min; Heating time: 10 min; Temperature: 100° C.; Pressure: 175 psi; Stirring: on; Cooling: on). At the end of the microwave irradiation cycle, the solvent was removed under reduced pressure. The crude product was purified by flash chromatography on silica gel (petroleum ether/ethyl acetate=90/10) to obtain 2-amino-4-phenyl-6-methylnicotinonitrile in 40% yield.

2) A catalytic amount of MTO (6 mg, 0.025 mmol) and excess 30% hydrogen peroxide (732 μl, 7.17 mmol) were added to a solution of 2-amino-4-phenyl-6-methylnicotinonitrile (100 mg, 0.48 mmol) in ethanol (5 ml). The reaction mixture was stirred for 17 h at room temperature. A catalytic amount of manganese dioxide was added to quench the excess peroxide. The mixture was then filtered and the solvent was removed with a rotary evaporator. The crude product was dissolved into water and extracted with methylene chloride. The organic phase was dried over anhydrous sodium sulphate and concentrated at reduced pressure. The crude product was purified by flash chromatography on silica gel (methylene chloride/methanol=98/2) thus obtaining 2-amino-4-phenyl-6-methylnicotinonitrile is N-oxide in 50% yield.

3) A suspension of 2-amino-4-phenyl-6-methylnicotinonitrile N-oxide (40 mg, 0.18 mmol) in 10% KOH (15 ml) was refluxed for 22 h. The reaction mixture was concentrated under reduced pressure and the resulting aqueous solution (5 ml) was washed with methylene chloride, acidified (pH=1) with concentrated hydrochloric acid and extracted with ethyl acetate. The organic phase was dried over anhydrous sodium sulphate; the solvent was evaporated at reduced pressure. The solid product was minced in hexane, filtered and dried to obtain 2-amino-4-phenyl-6-methylnicotinic acid N-oxide (I₅) as a white powder.

Yield: 35%

¹H-NMR (CD₃OD): δ 7.36 ppm (m, 5 H), 6.64 ppm (s, H), 3.50 ppm (s, 3 H, CH₃).

Example 6

Preparation of 2-amino-4,6-diisopropylnicotinic acid N-oxide (I₆):

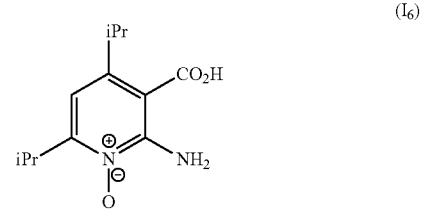

(I₆)

1) Isobutyraldehyde (370 μl, 4 mmol), isopropyl methyl ketone (250 μl, 4 mmol), malononitrile (264 mg, 4 mmol) e ammonium acetate (462 mg, 6 mmol) were placed in a microwave tube and irradiated with microwaves (Solvent: none; Power: 250 W; Ramp time: 1 min; Heating time: 10 min; Temperature: 100° C.; Pressure: 250 psi; Stirring: on; Cooling: on). At the end of the microwave irradiation cycle, the solvent was removed under reduced pressure. The crude product was purified by flash chromatography on silica gel (methylene chloride/methanol=90/10) to obtain 2-amino-4,6-diisopropylnicotinonitrile in 50% yield.

2) A catalytic amount of MTO (21 mg, 0.09 mmol) and excess 30% hydrogen peroxide (2.64 ml, 25.8 mmol) were added to a solution of 2-amino-4,6-diisopropylnicotinonitrile (350 mg, 1.72 mmol) in ethanol (10 ml). The reaction mixture was stirred for 1.5 h at room temperature. A catalytic amount of manganese dioxide was added to quench the excess peroxide. The mixture was then filtered and the solvent was removed with a rotary evaporator. The crude is product was dissolved into water and extracted with methylene chloride. The organic layer was dried over anhydrous sodium sulphate and concentrated at reduced pressure. The crude product was purified by flash chromatography on silica gel (methylene chloride/methanol=90/10) thus obtaining 2-amino-4,6-diisopropylnicotinonitrile N-oxide in 50% yield.

3) 2-Amino-4,6-diisopropylnicotinonitrile N-oxide (40 mg, 0.18 mmol) in 10% KOH (15 mL) was refluxed for 18 h. The reaction mixture was concentrated under reduced pressure and the resulting aqueous solution (5 ml) was washed with methylene chloride, acidified (pH=1) with concentrated hydrochloric acid and extracted with ethyl acetate. The organic phase was dried over anhydrous sodium sulphate; the solvent was evaporated at reduced pressure. The solid product was minced in hexane, filtered and dried to obtain 2-amino-4,6-diisopropylnicotinic acid N-oxide ($I_6$) in 45% yield.

$^1$H-NMR ($CD_3OD$): δ=6.74 ppm (s, H), 3.69 ppm (m, 2 H, J=6.6 Hz), 1.27 ppm (d, 6H, J=6.6 Hz), 1.33 ppm (d, 6H, J=6.6 Hz)

Example 7

In vitro Evaluation of the Biological Activity of the Compounds of Examples 1-6 by 3-hydroxyanthranilate-3,4-dioxygenase (3HAO) Inhibition in Rat The following procedure has been carried out for all the six compounds prepared according to the Examples 1-6 above.

One hundred μl of control Sprague Dawley rat brain homogenate (1/10 dilution in bidistilled water) were further diluted (1/2.5 v/v) with a 5 mM MES/NaOH buffer (pH 6.5) and incubated at 37° C. for 1 h in the presence of the radiolabeled substrate [14C]-3-hydroxyanthranilic acid (3.7 μM), ferrous ammonium sulphate (150 μM), ascorbic acid (0.01%). 20 μl of a solution (10 μM) of a compound of the invention were added prior to the addition of the radiolabeled substrate, for a total volume of 200 μl. The enzymatic reaction was stopped by adding 50 μl of 6% perchloric acid. The mixture was centrifuged for 5 min a 12.000 g and the supernatant was applied to a column packed with a cation-exchange resin (Dowex 50W, 0.5×2.0 cm; protonated form). [14C]-quinolinic acid formed by enzymatic reaction was eluted with 1 ml of distilled water. The eluate was added to scintillation liquid (Beckman, Ultima Gold) and radioactivity was measured with a is beta-counter.

The same procedure has been repeated by adding 20 μl of a solution (100 μM) of a compound of the invention and repeated by adding 20 μl of a solution (1000 μM) of a compound of the invention.

Results

The results obtained for each one of the three compounds of Examples 1-3, i.e. $I_1$-$I_3$, at the three concentrations used, i.e. 10 μM, 100 μM and 1000 μM, are reported below:

| In vitro 3HAO inhibition in rat (r) brain homogenates | | | |
|---|---|---|---|
| | % inibition of 3HAO (r) | | |
| Compound | 10 μM | 100 μM | 1000 μM |
| $I_1$ | 49 | 90 | 97 |
| $I_2$ | 22 | 76 | 99 |
| $I_3$ | 78 | 97 | 99 |

The results obtained for each one of the three compounds of Examples 4-6, i.e. $I_4$-$I_6$, at the concentration of 1000 μM are reported below:

| In vitro 3HAO inhibition in rat (r) brain homogenates | |
|---|---|
| | % inibition of 3HAO (r) |
| Compound | 1000 μM |
| $I_4$ | 15 |
| $I_5$ | 80 |
| $I_6$ | 70 |

The results demonstrated that compounds of Examples 1-6 of the present invention inhibited the activity of the 3-hydroxyanthranilate-3,4-dioxygenase (3HAO) enzyme and that such an inhibitory activity was surprisingly appreciable even at very low concentrations.

In particular, it can also be appreciated that the inhibitory activity of compounds $I_1$-$I_3$ reflects $IC_{50}$s in the low micromolar range, a value which is comparable with the Km of the natural substrate. Without wishing to be bound by any theory, it was believed that said data suggested the existence of a SAR (Structure-activity relationship) in which electron donating substituents in 6-position are more active than electron withdrawing ones.

These results, together with the reported data on the chemical stability of the following Example 10, allow to affirm that the compounds of the invention show the suitable features for in vivo systemic administration in animal models as well as in humans.

Example 8

In vitro Evaluation of the Biological Activity of the Compounds of Examples 1-6 by 3-hydroxyanthranilate-3,4-dioxygenase (3HAO) Inhibition in human The following procedure has been carried out for all the six compounds prepared according to the Examples 1-6 above.

One hundred μl of healthy human brain homogenate (1/10 dilution in bidistilled water) were further diluted (1/2.5 v/v) with a 5 mM MES/NaOH buffer (pH 6.5) and incubated at 37° C. for 1 h in the presence of the radiolabeled substrate [14C]-3-hydroxyanthranilic acid (3.7 μM), ferrous ammonium sulphate (150 μM), ascorbic acid (0.01%). 20 μl of a solution (10 μM) of a compound of the invention were added prior to the addition of the radiolabeled substrate, to a final volume of 200 μl. The enzymatic reaction was stopped by adding 50 μl of 6% perchloric acid. The mixture was centrifuged for 5 min a 12.000 g and the supernatant was applied to a column packed with a cation-exchange resin (Dowex 50W, 0.5×2.0 cm; protonated form). [14C]-quinolinic acid formed by enzymatic reaction was eluted with 1 ml of distilled water. The eluate was added to scintillation liquid (Beckman, Ultima Gold) and radioactivity was measured with a beta-counter.

The same procedure has been repeated by adding 20 μl of a solution (100 μM) of a compound of the invention and repeated by adding 20 μl of a solution (1000 μM) of a compound of the invention.

Results

The results obtained for each one of the three compounds of Examples 1-3, i.e. $I_1$-$I_3$, at the three concentrations used, i.e. 10 μM, 100 μM e 1000 μM, are reported below:

| In vitro 3HAO inhibition in human (h) brain homogenates | | | |
| --- | --- | --- | --- |
| | % inibition of 3HAO (h) | | |
| Compound | 10 μM | 100 μM | 1000 μM |
| $I_1$ | 66 | 93 | 96 |
| $I_2$ | 42 | 100 | 100 |
| $I_3$ | 80 | 100 | 100 |

The results obtained for each one of the three compounds of Examples 4-6, i.e. $I_4$-$I_6$, at the concentration of 1000 μM are reported below:

| In vitro 3HAO inhibition in human (h) brain homogenates | |
| --- | --- |
| Compound | % inibition of 3HAO (h) 1000 μM |
| $I_4$ | 23 |
| $I_5$ | 70 |
| $I_6$ | 60 |

The results obtained with the human brain homogenate confirmed those obtained in rat and further demonstrated that compounds of Examples 1-6 of the present invention inhibited the activity of the 3-hydroxyanthranilate-3,4-dioxygenase (3HAO) enzyme and that such an inhibitory activity was also surprisingly appreciable even at very low concentrations.

In particular, it can also be appreciated that the inhibitory activity of compounds $I_1$-$I_3$ reflects $IC_{50}$s in the low micromolar range, a value which is comparable with the Km of the natural substrate. Without wishing to be bound by any theory, it was believed that said data suggested the existence of a SAR (Structure-activity relationship) in which electron donating substituents in 6-position are more active than electron withdrawing ones.

These results, together with the reported data on the chemical stability of the following Example 10, allow to affirm that the compounds of the invention show the is suitable features for in vivo systemic administration in animal models as well as in humans.

Example 9

In vivo Evaluation of the Activity of the Compound $I_3$ in QUIN-lesioned Rat Brain after Administration under Excitotoxic Conditions Quinolinic acid lesions in the rat striatum were made as described by Schwarcz et al. (1983), using 300 nmol quinolinic acid per injection. In vivo assays of $I_3$ in the lesioned striatum were performed 7 days later. [Schwarcz R, Whetsell W O Jr, Mangano R M (1983) Quinolinic acid: an endogenous metabolite that produces axon-sparing lesions in rat brain. Science 219:316-8.]

Intrastriatal injection of 3H-kynurenine: two months-old male Sprague-Dawley rats were anesthetized with chloral hydrate (360 mg/kg, i.p.) and mounted in a David Kopf stereotaxic apparatus (Tujunga, Calif.). Through a small burr hole in the skull, 2.5 mCi of 3H-kynurenine [in phosphate-buffered saline (PBS), pH 7.4] was infused (6 μL over 10 min) intrastriatally. 3H-kynurenine was infused in the absence or presence of 5 mM $I_3$. The injection coordinates were: AP: 1.0 mm anterior to bregma, L: 2.6 mm from the midline, V: 4.8 mm below dura. Animals were euthanized 2 h later and the striatum was dissected out, frozen on dry ice and stored at −80° C. Subsequently, the tissue was processed for the determination of tritiated neuroactive products of KP metabolism. [Amori L, Guidetti P, Pellicciari R, Kajii Y, Schwarcz R (2009) On the relationship between the two branches of the kynurenine pathway in the rat brain in vivo. J Neurochem 109:316-25.]

Analysis of 3H-quinolinic acid: the analysis of tritiated quinolinic acid derived from 3H-kynurenine was performed essentially as described by Guidetti et al. (1995). [Guidetti P, Eastman C L, Schwarcz R (1995) Metabolism of [5-3H] kynurenine in the rat brain in vivo: evidence for the existence of a functionalkynurenine pathway. J Neurochem 65:2621-32.] Briefly, the thawed striatal tissue was homogenized (1:10, w/v) in ultrapure water, and the homogenate was deproteinized using 6% is perchloric acid. After removal of the precipitated proteins using a centrifuge (13,700×g, 15 min), 100 μL of the acidic supernatant were applied to a C18 reverse-phase HPLC column (Lichrosorb; 250×4.6 mm; Alltech Assoc.) and eluted at a flow rate of 1.2 ml/min using a mobile phase consisting of 100 mM $(NH_4)H_2PO_4$ and 100 mM acetic acid (titrated to pH 3.2 with phosphoric acid), containing 1.25 mM octane sulfonic acid and 6% acetonitrile. Tritiated quinolinic acid was detected radiometrically (Beta-Ram; IN/US Systems, Tampa, Fla.). The retention time of quinolinic acid was approximately 2.5 min. As reported in FIG. 1, compound $I_3$ is able to block the abnormal de novo production of QUIN under excitotoxic conditions, thus restoring the QUIN physiological level, an indication for the use of compound I3 as an agent preventing QUIN-induced neurotoxicity.

Example 10

Evaluation of the Chemical Stability of the Compound $I_3$ over Time

Figure 2:
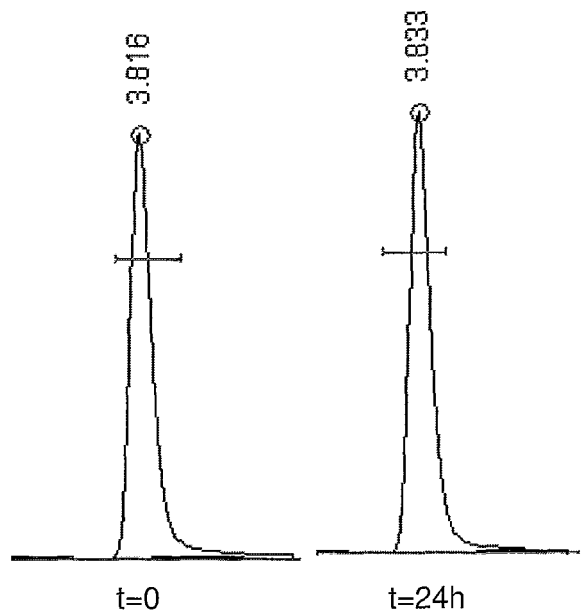
FIG. 2 shows a chemical stability evaluation of the compound of Example 3, over the time.

Compound $I_3$ was dissolved in a phosphate buffer at pH 7.5 at two different concentrations (10 and 100 μM). The resulting solutions were incubated at 37° C. for 24 h. The HPLC analysis of the solutions, before (t=0) and after (t=24 h) the incubation, showed complete chemical stability of compound $I_3$, as clearly demonstrated in FIG. 2, where the HPLC chromatograms have been reported, at t=0 (left) and at t=24 h (right).

Chromatographic analyses were performed with a HPLC system (Shimadzu Corp., Kyoto, Japan), endowed with a UV/VIS detector, and the samples were eluted with a mixture containing methanol (0.05% TFA)/water (0.25% TFA)=20/80 at a flow rate of 1 ml/min.

\* \* \*

From the above description and the above-noted Examples, the advantages attained by the product described and obtained according to the present invention are apparent. Specifically, the compounds, subject of the present invention, act as inhibitors of enzyme 3-hydroxyanthranilate-3,4-dioxygenase (3HAO), and are thus able to reduce QUIN biosynthesis in vivo under excitotoxic or pathological conditions, said compounds being at the same time also chemically stable towards auto-oxidation.

The invention claimed is:

1. A method for inhibiting activity of 3-hydroxyanthranilate-3,4-dioxygenase (3HAO), the method comprising:
administering a compound of formula (I):

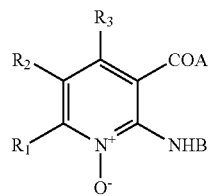

(I)

wherein
$R_1$, $R_2$, $R_3$ are, independently of each other, H, halogen or a $C_1$-$C_6$ alkyl group,
A is —OH and
B is H in a therapeutic amount to treat pathologies ascribable to an excessive quinolinic acid (QUIN) production.

2. The method of claim 1, wherein the pathologies are Alzheimer's disease, Huntington's disease, cerebral ischemia, HIV-related dementia or neonatal hypoxia.

3. The method of claim 1, wherein the compound is formula ($I_3$)

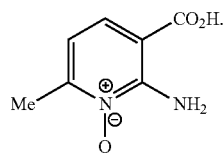

4. The method of claim 1, wherein the compound is formula ($I_1$):

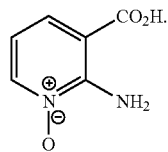

($I_1$)

5. The method of claim 1, wherein the compound is formula ($I_2$):

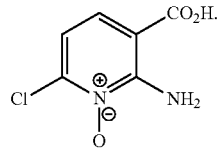

($I_2$)

6. A method for reducing levels of quinolinic acid (QUIN), the method comprising:
administering to a subject in need thereof a compound of formula (I):

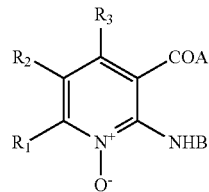

(I)

wherein
$R_1$, $R_2$, $R_3$ are, independently of each other, H, halogen or a $C_1$-$C_6$ alkyl group,
A is —OH and
B is H in a therapeutic amount to reduce QUIN-induced neurotoxicity.

* * * * *